United States Patent [19]

Fäh

[11] Patent Number: 4,587,353
[45] Date of Patent: May 6, 1986

[54] PROCESS FOR PRODUCING N-CHLOROSULFENYL COMPOUNDS

[75] Inventor: Hansjakob Fäh, Ormalingen, Switzerland

[73] Assignee: Ciba-Geigy Corporation, Ardsley, N.Y.

[21] Appl. No.: 525,598

[22] Filed: Aug. 23, 1983

[51] Int. Cl.⁴ .................. C07C 161/00; C07D 307/86
[52] U.S. Cl. .................................... 549/470; 560/147; 560/148; 564/483
[58] Field of Search ................ 549/470; 560/147, 148; 564/483

[56] References Cited

U.S. PATENT DOCUMENTS

| | | | |
|---|---|---|---|
| 3,843,689 | 10/1974 | Brown et al. | 549/470 |
| 4,333,883 | 6/1982 | Nelson | 260/544 C |
| 4,421,693 | 12/1983 | Goto et al. | 549/470 |

FOREIGN PATENT DOCUMENTS

| | | |
|---|---|---|
| 0051273 | 5/1982 | European Pat. Off. |
| 1583713 | 1/1981 | United Kingdom |
| 2084134 | 4/1982 | United Kingdom |

Primary Examiner—Henry R. Jiles
Assistant Examiner—Bernard I. Dentz
Attorney, Agent, or Firm—Karl F. Jorda

[57] ABSTRACT

There is described a process for producing N-chlorosulfenyl compounds of the formula

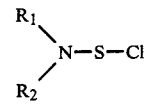

in which $R_1$ is alkyl, alkoxycarbonyl, alkoxycarbonylalkyl or 2,3-dihydro-2,2-dimethylbenzofuran-7-yloxycarbonyl, and $R_2$ is alkyl or alkoxycarbonylalkyl, which process is based on the reaction of an amino compound of the formula

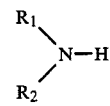

with sulfur dichloride. The essential feature of the process is that the reaction of the amino compound of the above formula with the sulfur dichloride is performed in excess sulfur dichloride as solvent and in the absence of a base. The formed N-chlorosulfenyl compounds of the above formula are intermediates for insecticidal and acaricidal active substances.

8 Claims, No Drawings

PROCESS FOR PRODUCING N-CHLOROSULFENYL COMPOUNDS

The present invention relates to a process for producing N-chlorosulfenyl compounds of the formula

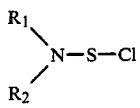

in which $R_1$ is $C_1$–$C_8$-alkyl, $C_1$–$C_8$-alkoxycarbonyl, $C_1$–$C_8$-alkoxycarbonyl-$C_1$–$C_6$-alkyl or 2,3-dihydro-2,2-dimethylbenzofuran-7-yloxycarbonyl, and $R_2$ is $C_1$–$C_8$-alkyl or $C_1$–$C_8$-alkoxycarbonyl-$C_1$–$C_6$-alkyl.

The N-chlorosulfenyl compounds of the formula I are intermediates for producing N,N-sulfides which are distinguished by a marked insecticidal and acaricidal action. To be mentioned as active substances of this kind are for example: 2,3-dihydro-2,2-dimethylbenzofuran-7-yl-N-methyl-N-(N-methyl-N-butoxycarbonylaminosulfenyl)-carbamate, 2,3-dihydro-2,2-dimethylbenzofuran-7-yl-N-methyl-N-(N,N-dibutylaminosulfenyl)-carbamate and 2,3-dihydro-2,2-dimethylbenzofuran-7-yl-N-methyl-N-(N-ethoxycarbonylethyl-N-isopropylaminosulfenyl)-carbamate.

Such insecticidal active substances, the production thereof and their use are described for example in the British Patent Specification Nos. 1,583,713 and 2,084,134, and in the U.S. Pat. No. 4,006,231.

It is known that N-chlorosulfenyl compounds can be produced from carbamates by dissolving the carbamate and the essentially equivalent amount of sulfur dichloride in an inert solvent, for example methylene chloride, and feeding into this solution a base, for example pyridine, in controlled amounts. After completion of the reaction, the hydrochloride of the base is filtered off; the solvent is then distilled off and the crude product purified by distillation (cp. U.S. Pat. No. 3,843,688).

Also known is the method of producing N-chlorosulfenyl compounds from carbamoyl halides by taking the carbamoyl halide and sulfur dichloride in a molar ratio of 1:2, and introducing into this mixture, with cooling, a base, such as a tert-alkylamine, pyridine or lutidine. After the reaction has finished, the bulk of the unreacted sulfur dichloride is distilled off, and from the residue is then obtained a crude product by further distillation, this product containing, besides the desired N-chlorosulfenylcarbamoyl halide, considerable amounts of sulfur monochloride ($S_2Cl_2$) and a small amount of sulfur dichloride. From this crude product is obtained pure N-chlorosulfenylcarbamoyl halide by chlorinating the sulfur monochloride to sulfur dichloride, and separating this by distillation (cp. U.S. Pat. No. 4,333,883).

Finally, it is also known that N-chlorosulfenyl compounds can be produced from dialkylamines by firstly converting a dialkylamine by reaction with sulfur monochloride into the corresponding N,N-disulfide, and subsequently converting this by reaction with a chlorinating agent, such as chlorine or sulfuryl chloride, into the corresponding dialkylaminosulfenyl chloride (cp. European Patent Application No. 0,051,273).

According to the present invention, a process for producing N-chlorosulfenyl compounds of the formula I is suggested, which is based on the reaction of an amino compound of the formula II

in which $R_1$ and $R_2$ have the meanings defined under the formula I, with sulfur dichloride, which process comprises performing the reaction of the amino compound of the formula II with sulfur dichloride at 10°–60° C., in excess sulfur dichloride as solvent and in the absence of a base, and obtaining the N-chlorosulfenyl compound of the formula I by evaporating off the unreacted sulfur dichloride.

The process according to the invention is advantageously performed by taking the sulfur dichloride and slowly adding the amino compound of the formula II in controlled amounts. The excess of sulfur dichloride can vary within wide limits, with no critical upper limit existing with regard to the technical practicability of the process. The limit is therefore determined primarily by economic factors. In the carrying out of the process according to the invention, there can thus be used as a rule 1.25–10.0 mols of sulfur dichloride per mol of the amino compound of the formula II. There are used advantageously 1.5–5.0 mols of sulfur dichloride per mol of the amino compound of the formula II, and particularly advantageously 1.6–2.0 mols of sulfur dichloride per mol of amino compound of the formula II.

Within the given temperature range of 10°–60° C., in which the process according to the invention can be performed, temperatures of 25°–50° C. and especially temperatures of 30°–40° C. are preferred.

After the completed reaction of the amino compound of the formula II with the sulfur dichloride, the distilling off of the excess sulfur dichloride can be performed at normal pressure or under reduced pressure. In order to avoid high temperatures, and in view of the fact that sulfur dichloride (boiling point: 59° C.) readily decomposes with the formation of sulfur monochloride ($S_2Cl_2$; boiling point: 139° C.) and chlorine, it is advantageous to distill off the excess sulfur dichloride at the lowest possible temperature under reduced pressure, for example under a pressure of 100–300 mbar.

The sulfur dichloride distilled off from the reaction mixture can be recycled and used for a further reaction with an amino compound of the formula II. Since also with distillation under reduced pressure, the sulfur dichloride partially decomposes into sulfur monochloride and chlorine, it is necessary before recycling to treat the resulting distillate with a chlorinating agent, such as chlorine gas or sulfuryl chloride, in order to convert the sulfur monochloride present into sulfur dichloride. For this chlorination it is also possible to re-use the chlorine formed during decomposition of sulfur dichloride.

The N-chlorosulfenyl compounds of the formula I obtained after the excess sulfur dichloride has been distilled off are already of high purity, and can therefore as a rule be used directly for further reaction to give an insecticidal active substance. If necessary, however, the N-chlorosulfenyl compounds of the formula I can also be purified by distillation before they are further processed.

The process according to the invention can be carried out either discontinuously (batchwise) or continuously.

It is suitable in particular for continous operation since the sulfur dichloride distilled off from the reaction mixture can be recycled, after a chlorination treatment, for further use in the process.

The process according to the invention is suitable for producing the N-chlorosulfenyl compounds of the formula I on a commercial scale in a simple manner and in good yield and quality. Compared with known processes, the process according to the invention is distinguished particularly by the simplicity of the further processing of the reaction mixture obtained after completion of the reaction of an amino compound of the formula II with excess sulfur dichloride. This further processing is limited to a simple distillation since neither a salt of a base nor an organic solvent has to be separated off. The recovery, necessary in the prior known processes, of the base used as an acid-binding agent, and also the purification of the base and of the organic solvent, are thus avoided. The mixture of sulfur dichloride and sulfur monochloride, obtained on final distillation, can be converted in a simple manner, by treatment with a chlorinating agent, into directly re-usable sulfur dichloride. By application of the procedure according to the invention, side reactions are largely avoided, and the N-chlorosulfenyl compounds of the formula I are obtained in excellent yield and with a high degree of purity.

The process according to the invention is further illustrated by the following Examples.

EXAMPLE 1

Production of n-butyl-(N-methyl-N-chlorosulfenyl)carbamate 280 kg (2.7 kilomols) of sulfur dichloride are placed into a 630 liter enameled vessel, and at 30° C. are added in controlled amounts from a feed vessel, within 5 hours, 196.5 kg (1.5 kilomols) of n-butyl-N-methyl carbamate. After completion of the addition, the internal temperature is raised stepwise to 40° C. and is held there for 3 hours. There are subsequently distilled off at 40° C. and 200 mbar 120 kg of sulfur dichloride and formed sulfur monochloride. The crude n-butyl-(N-methyl-N-chlorosulfenyl)-carbamate obtained as residue is purified by distillation under high vacuum (0.5 mbar; 74°–76° C.). There are obtained 255.0 kg of 97–98% pure n-butyl-(N-methyl-N-chlorosulfenyl)-carbamate, the yield being 85% of theory, relative to the employed n-butyl-N-methyl carbamate.

The mixture of sulfur dichloride and sulfur monochloride distilled off from the reaction mixture is converted, by the introduction of 40.0 kg of chlorine at 0°–5° C., again into sulfur dichloride, which can be used for further reactions.

In a manner analogous to that described in Example 1, the following amino compounds of the formula II are converted into the corresponding N-chlorosulfenyl compounds of the formula I:
di-n-butylamine,
N-(2-ethoxycarbonylethyl)-isopropylamine,
2,3-dihydro-2,2-dimethylbenzofuran-2-yl-N-methyl carbamate,
di-n-octylamine,
n-propyl-N-ethyl carbamate,
methyl-N-n-butyl carbamate,
N-ethoxycarbonylmethyl-methylamine,
bis-(methoxycarbonylmethyl)-amine,
bis-(methoxycarbonylethyl)-amine,
ethyl-N-methyl carbamate,
n-octyl-N-methyl carbamate, and
ethyl-N-isopropyl carbamate.

What is claimed is:

1. In a process for producing an N-chlorosulfenyl compound of the formula

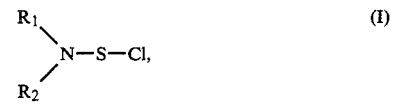

in which $R_1$ is $C_1$–$C_8$-alkyl, $C_1$–$C_8$-alkoxycarbonyl, $C_1$–$C_8$-alkoxycarbonyl-$C_1$–$C_6$-alkyl or 2,3-dihydro-2,2-dimethylbenzofuran-7-yloxycarbonyl, and $R_2$ is $C_1$–$C_8$-alkyl or $C_1$–$C_8$-alkoxycarbonyl-$C_1$–$C_6$-alkyl, by reaction of an amino compound of the formula II

in which $R_1$ and $R_2$ have the meanings defined under the formula I, with sulfur dichloride, the improvement which comprises performing the reaction of the amino compound of the formula II with sulfur dichloride at 10°–60° C., in excess sulfur dichloride as solvent and in the absence of a base, and obtaining the formed N-chlorosulfenyl compound of the formula I by evaporating off the unreacted sulfur dichloride.

2. A process according to claim 1, wherein 1.25–10.0 mols of sulfur dichloride are used per mol of the amino compound of the formula II.

3. A process according to claim 1, wherein 1.5–5.0 mols of sulfur dichloride are used per mol of the amino compound of the formula II.

4. A process according to claim 3, wherein 1.6–2.0 mols of sulfur dichloride are used per mol of the amino compound of the formula II.

5. A process according to claim 1, wherein the sulfur dichloride is placed into the reaction vessel and the amino compound of the formula II is slowly added in controlled amounts.

6. A process according to claim 1, wherein the reaction of the sulfur dichloride with the amino compound of the formula II is performed at a temperature of 25°–50° C.

7. A process according to claim 6, wherein the reaction of the sulfur dichloride with the amino compound of the formula II is performed at a temperature of 30°–40° C.

8. A process according to claim 1, wherein, after the reaction of the sulfur dichloride with the amino compound of the formula II, the unreacted sulfur dichloride is distilled off under reduced pressure from the reaction mixture.

* * * * *